(12) United States Patent
Huang et al.

(10) Patent No.: US 11,338,019 B2
(45) Date of Patent: May 24, 2022

(54) RECOMBINANT THROMBOMODULIN DOMAIN 1 FOR USE IN TREATING EYE DISEASES ASSOCIATED WITH PATHOLOGICAL OCULAR ANGIOGENESIS

(71) Applicants: Yi-Hsun Huang, Tainan (TW); Hua-Lin Wu, Taipei (TW)

(72) Inventors: Yi-Hsun Huang, Tainan (TW); Hua-Lin Wu, Taipei (TW)

( * ) Notice: Subject to any disclaimer, the term of this patent is extended or adjusted under 35 U.S.C. 154(b) by 0 days.

(21) Appl. No.: 16/882,508

(22) Filed: May 24, 2020

(65) Prior Publication Data

US 2021/0361747 A1 Nov. 25, 2021

(51) Int. Cl.
| | | |
|---|---|---|
| A61K 38/36 | (2006.01) |
| A61K 38/18 | (2006.01) |
| A61P 27/02 | (2006.01) |
| A61K 38/17 | (2006.01) |
| A61K 9/00 | (2006.01) |
| A61K 9/06 | (2006.01) |

(52) U.S. Cl.
CPC ........ *A61K 38/366* (2013.01); *A61K 38/1783* (2013.01); *A61K 38/1866* (2013.01); *A61P 27/02* (2018.01); *A61K 9/0014* (2013.01); *A61K 9/0019* (2013.01); *A61K 9/0048* (2013.01); *A61K 9/06* (2013.01)

(58) Field of Classification Search
CPC .... A61K 38/366; A61K 38/1866; A61P 27/02
See application file for complete search history.

(56) References Cited

U.S. PATENT DOCUMENTS

| | | | | |
|---|---|---|---|---|
| 7,803,367 B2* | 9/2010 | Wu | ........................ | A61K 48/00 424/94.3 |
| 8,293,231 B2* | 10/2012 | Wu | ........................... | A61P 9/10 424/94.64 |
| 9,775,885 B2 | 10/2017 | Cheng et al. | | |
| 2006/0148695 A1* | 7/2006 | Wu | ........................ | A61K 48/00 530/210 |
| 2009/0118189 A1* | 5/2009 | Wu | ...................... | A61K 38/366 514/6.9 |
| 2010/0303800 A1* | 12/2010 | Wu | ........................... | A61P 9/10 424/94.64 |
| 2012/0165244 A1* | 6/2012 | Wu | ........................ | A61P 13/12 514/1.4 |
| 2017/0007681 A1* | 1/2017 | McCarty | ................. | A61P 29/00 |

FOREIGN PATENT DOCUMENTS

WO 2002096947 A2 12/2002

OTHER PUBLICATIONS

Montassar et al., 2017, Lebecetin, a C-type lectin, inhibits choroidal and retinal neovascularization, FASEB J, 31: 1107-1119.*
Kauppinen et al., 2016, Inflammation and its role in age-related macular degeneration, Cell Mol Life Sci, 73: 1765-1786.*
Rubsam et al., 2018, Role of Inflammation in Diabetic Retinopathy, International Journal of Molecular Sciences, 19: 942 (31 pages).*
Wang et al., 2014, Recombinant Thrombomodulin of Different Domains for Pharmaceutical, Biomedical, and Cell Transplantation Applications, Medicinal Research Reviews, 34(3): 479-502.*
Miller et al., 1994, Vascular Endothelial Growth Factor/Vascular Permeability Factor Is Temporally and Spatially Correlated with Ocular Angiogenesis in a primate Model, American Journal of Pathology, 145(3): 574-584.*
Shima et al., 1995, Hypoxia Induction of Endothelial Cell Growth Factors in Retinal Cells: Identification and Characterization of Vascular Endothelial Growth Factor (VEGF) as the Mitogen, Molecular Medicine, 1(2): 182-193.*
Rubio et al., 2016, Ocular Angiogenesis: Vascular Endothelial Growth Factor and Other Factors, Dev Ophthalmol, 55: 28-37.*
Mesquita et al., 2018, Vascular endothelial growth factors and placenta growth factor in retinal vasculopathies: Current research and future perspectives, Cytokine and Growth Factor Reviews, 39: 102-115.*
Lin et al., 2013, Recombinant Lectin-Like Domain of Thrombomodulin Suppresses Vascular Inflammation by Reducing Leukocyte Recruitment via Interacting With Lewis Y on Endothelial Cells, Arterioscler Thromb Vasc Biol, 33: 2366-2373.*
Kuo et al., 2012, The recombinant lectin-like domain of thrombomodulin inhibits angiogenesis through interaction with Lewis Y antigen, Blood, 119(5): 1302-1313.*
Shi et al. "Lectin-ike Domain of Thrombomodulin Binds to its Specific Ligand Lewis Y Antigen and Neutralizes Lipopolysaccharide-Induced Inflammatory Response" Blood. 2008:112:3661-3670.
Lains et al. "Choroidal Thickness in Diabetic Retinopathy: The Influence of Antiangiogenic Therapy" Retina. Jun. 2014;34(6):1199-207.
Conway et al. "The Lectin-like Domain of Thrombomodulin Confers Protection from Neutrophil-mediated Tissue Damage by Suppressing Adhesion Molecule Expression via Nuclear Factor kB and Mitogen-activated Protein Kinase Pathways" J. Exp. Med. vol. 196, No. 5, Sep. 2, 2002 565-577.

(Continued)

*Primary Examiner* — Amber D Steele
(74) *Attorney, Agent, or Firm* — Hsiu-Ming Saunders; Intellectual Property Connections, Inc.

(57) ABSTRACT

The present application relates to dual anti-angiogenic and anti-inflammatory effects of recombinant thrombomodulin domain 1 (TMD1). Specifically, an isolated recombinant polypeptide comprising an amino acid sequence that is at least 80% identical to TMD1 for use in treating an eye disease and/or an eye disorder associated with pathological ocular angiogenesis (POA) in a subject in need thereof is disclosed. The length of the recombinant polypeptide is no more than 200 amino acid residues. The eye disease and/or the eye disorder may be at least one selected from the group consisting of retinopathy of prematurity, diabetic retinopathy, and age-related macular degeneration. Use of TMD1 in the manufacture of a medicament for treating an eye disease and/or an eye disorder associated with vascular endothelial growth factor (VEGF)-induced ocular angiogenesis and/or hypoxia-inducible factor-1α (HIF-1α)-VEGF pathway is also disclosed.

7 Claims, 6 Drawing Sheets

Specification includes a Sequence Listing.

(56) References Cited

OTHER PUBLICATIONS

Li et al. "The role of thrombomodulin lectin-like domain in inflammation" Journal of Biomedical Science 2012, 19:34.
Kuo et al. "The recombinant lectin-like domain of thrombomodulin inhibits angiogenesis through interaction with LewisYantigen" Blood. 2012:119(5):1302-1313.
Cheng et al. "Myeloid thrombomodulin lectin-like domain inhibits osteoclastogenesis and inflammatory bone loss" Sci. Rep. 6, 28340; doi: 10.1038/srep28340 (2016).

* cited by examiner

SEQUENCE LISTING

<160> NUMBER OF SEQ ID NOS: 4

<210> SEQ ID NO 1
<211> LENGTH: 155
<212> TYPE: PRT
<213> ORGANISM: Homo sapiens

<400> SEQUENCE: 1

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Cys Glu Val Lys Ala
    130                 135                 140

Asp Gly Phe Leu Cys Glu Phe His Phe Pro Ala
145                 150                 155

<210> SEQ ID NO 2
<211> LENGTH: 465
<212> TYPE: DNA
<213> ORGANISM: Homo sapiens

<400> SEQUENCE: 2
gcacccgcag agccgcagcc gggtggcagc cagtgcgtcg agcacgactg cttcgcgctc      60
tacccgggcc ccgcgacctt cctcaatgcc agtcagatct gcgacggact gcggggccac     120
ctaatgacag tgcgctcctc ggtggctgcc gatgtcattt ccttgctact gaacggcgac     180
ggcggcgttg gccgccggcg cctctggatc ggcctgcagc tgccacccgg ctgcggcgac     240
cccaagcgcc tcgggcccct gcgcggcttc cagtgggtta cgggagacaa caacaccagc     300
tatagcaggt gggcacggct cgacctcaat ggggctcccc tctgcggccc gttgtgcgtc     360
gctgtctccg ctgctgaggc cactgtgccc agcgagccga tctgggagga gcagcagtgc     420
gaagtgaagg ccgatggctt cctctgcgag ttccacttcc cagcc                     465

<210> SEQ ID NO 3
<211> LENGTH: 557
<212> TYPE: PRT
<213> ORGANISM: Homo sapiens

<400> SEQUENCE: 3

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

-continued

```
Ile Cys Asp Gly Leu Arg Gly His Leu Met Thr Val Arg Ser Ser Val
         35                  40                  45

Ala Ala Asp Val Ile Ser Leu Leu Asn Gly Asp Gly Gly Val Gly
 50                  55                  60

Arg Arg Arg Leu Trp Ile Gly Leu Gln Leu Pro Pro Gly Cys Gly Asp
 65                  70                  75                  80

Pro Lys Arg Leu Gly Pro Leu Arg Gly Phe Gln Trp Val Thr Gly Asp
                 85                  90                  95

Asn Asn Thr Ser Tyr Ser Arg Trp Ala Arg Leu Asp Leu Asn Gly Ala
             100                 105                 110

Pro Leu Cys Gly Pro Leu Cys Val Ala Val Ser Ala Ala Glu Ala Thr
             115                 120                 125

Val Pro Ser Glu Pro Ile Trp Glu Glu Gln Gln Cys Glu Val Lys Ala
         130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                 165                 170                 175

Thr Pro Phe Ala Ala Arg Gly Ala Asp Phe Gln Ala Leu Pro Val Gly
             180                 185                 190

Ser Ser Ala Ala Val Ala Pro Leu Gly Leu Gln Leu Met Cys Thr Ala
         195                 200                 205

Pro Pro Gly Ala Val Gln Gly His Trp Ala Arg Glu Ala Pro Gly Ala
         210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                 245                 250                 255

Ala Asp Gly Arg Ser Cys Thr Ala Ser Ala Thr Gln Ser Cys Asn Asp
             260                 265                 270

Leu Cys Glu His Phe Cys Val Pro Asn Pro Asp Gln Pro Gly Ser Tyr
         275                 280                 285

Ser Cys Met Cys Glu Thr Gly Tyr Arg Leu Ala Ala Asp Gln His Arg
         290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                 325                 330                 335

Tyr Asp Leu Val Asp Gly Glu Cys Val Glu Pro Val Asp Pro Cys Phe
             340                 345                 350

Arg Ala Asn Cys Glu Tyr Gln Cys Gln Pro Leu Asn Gln Thr Ser Tyr
             355                 360                 365

Leu Cys Val Cys Ala Glu Gly Phe Ala Pro Ile Pro His Glu Pro His
         370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                 405                 410                 415

Asp Gly Phe Ile Cys Thr Asp Ile Asp Glu Cys Glu Asn Gly Gly Phe
             420                 425                 430

Cys Ser Gly Val Cys His Asn Leu Pro Gly Thr Phe Glu Cys Ile Cys
         435                 440                 445
```

```
Gly Pro Asp Ser Ala Leu Val Arg His Ile Gly Thr Asp Cys Asp Ser
    450                 455                 460

Gly Lys Val Asp Gly Gly Asp Ser Gly Ser Gly Glu Pro Pro Pro Ser
465                 470                 475                 480

Pro Thr Pro Gly Ser Thr Leu Thr Pro Pro Ala Val Gly Leu Val His
                485                 490                 495

Ser Gly Leu Leu Ile Gly Ile Ser Ile Ala Ser Leu Cys Leu Val Val
                500                 505                 510

Ala Leu Leu Ala Leu Leu Cys His Leu Arg Lys Lys Gln Gly Ala Ala
            515                 520                 525

Arg Ala Lys Met Glu Tyr Lys Cys Ala Ala Pro Ser Lys Glu Val Val
530                 535                 540

Leu Gln His Val Arg Thr Glu Arg Thr Pro Gln Arg Leu
545                 550                 555

<210> SEQ ID NO 4
<211> LENGTH: 1671
<212> TYPE: DNA
<213> ORGANISM: Homo sapiens

<400> SEQUENCE: 4
gcacccgcag agccgcagcc gggtggcagc cagtgcgtcg agcacgactg cttcgcgctc      60
tacccgggcc ccgcgacctt cctcaatgcc agtcagatct cgacggact gcggggccac     120 ctaatgacag tgcgctcctc ggtggctgcc gatgtcattt ccttgctact gaacggcgac     180
ggcggcgttg ccgcgcggcg cctctggatc ggcctgcagc tgccaccgg ctgcggcgac      240 cccaagcgcc tcgggcccct cgcgcggcttc agtgggtta cgggagacaa caacaccagc     300
tatagcaggt gggcacggct cgacctcaat ggggctcccc tctgcggccc gttgtgcgtc     360
gctgtctccg ctgctgaggc cactgtgccc agcgagccga tctgggagga gcagcagtgc     420
gaagtgaagg ccgatggctt cctctgcgag ttccacttcc cagccacctg caggccactg     480
gctgtggagc ccggcgccgc ggctgccgcc gtctcgatca cctacggcac cccgttcgcg     540
gcccgcggag cggacttcca ggcgctgccg gtgggcagct ccgccgcggt ggctcccctc     600
ggcttacagc taatgtgcac cgcgccgccc ggagcggtcc aggggcactg gccagggag     660 gcgccgggcg cttgggactg cagcgtggag aacggcggct gcgagcacgc gtgcaatgcg     720
atccctgggg ctccccgctg ccagtgccca gccggcgccg ccctgcaggc agacgggcgc     780
tcctgcaccg catccgcgac gcagtcctgc aacgacctct gcgagcactt ctgcgttccc     840
aaccccgacc agccgggctc ctactcgtgc atgtgcgaga ccggctaccg gctggcggcc     900
gaccaacacc ggtgcgagga cgtggatgac tgcatactgg agcccagtcc gtgtccgcag     960
cgctgtgtca acacacaggg tggcttcgag tgccactgct accctaacta cgacctggtg    1020
gacggcgagt gtgtggagcc cgtggacccg tgcttcagag ccaactgcga gtaccagtgc    1080
cagcccctga ccaaactag ctacctctgc gtctgcgccg agggcttcgc gcccattccc    1140
cacgagccgc acaggtgcca gatgttttgc aaccagactg cctgtccagc cgactgcgac    1200
cccaacaccc aggctagctg tgagtgccct gaaggctaca tcctggacga cggtttcatc    1260
tgcacggaca tcgacgagtg cgaaaacggc ggcttctgct ccggggtgtg ccacaacctc    1320
cccggtacct tcgagtgcat ctgcgggccc gactcggccc ttgtccgcca cattggcacc    1380
gactgtgact ccggcaaggt ggacggtggc gacagcggct ctggcgagcc ccgcccagc    1440 ccgacgcccg gctccacctt gactcctccg gccgtggggc tcgtgcattc gggcttgctc    1500
```

| | | | | | |
|---|---|---|---|---|---|
| ataggcatct | ccatcgcgag | cctgtgcctg | gtggtggcgc | ttttggcgct | cctctgccac 1560 |
| ctgcgcaaga | agcagggcgc | cgccagggcc | aagatggagt | acaagtgcgc | ggcccctttcc 1620 |
| aaggaggtag | tgctgcagca | cgtgcggacc | gagcggacgc | cgcagagact | c 1671 |

RECOMBINANT THROMBOMODULIN DOMAIN 1 FOR USE IN TREATING EYE DISEASES ASSOCIATED WITH PATHOLOGICAL OCULAR ANGIOGENESIS

FIELD OF THE INVENTION

The present invention relates generally to recombinant thrombomodulin domain 1, and more specifically to recombinant thrombomodulin domain 1 for use in treating an eye disease and/or an eye disorder associated with pathological ocular angiogenesis.

BACKGROUND OF THE INVENTION

Pathologic ocular angiogenesis is the underlying mechanism of a variety of sight threatening diseases of the eye affecting a wide range of patients including premature infants and the elderly. Retinopathy of prematurity (ROP), proliferative diabetic retinopathy (PDR), and exudative age-related macular degeneration (wet AMD) are common causes of blindness in infants, working age, and the elderly respectively. Vascular endothelial growth factor (VEGF) is upregulated and secreted by tissues in response to hypoxia or inflammation, which is the major cause of pathological ocular angiogenesis (POA) and targeted in current anti-angiogenic therapies for neovascular eye diseases.

The anti-VEGF therapies have been effective in treating POA. VEGF is, however, also essential for normal physiological vessel growth. Thus, inhibition of VEGF can lead to significant adverse outcomes, especially in developing retinas in newborns. Bevacizumab, an antibody against VEGF, is effective in treating diabetic retinopathy (DR). The anti-VEGF agent bevacizumab can, however, lead to geographic atrophy and changes from angiogenesis to fibrosis after long-term anti-VEGF injections, which further results in tractional retinal detachments in patients with severe DR (Kuiper et al., 2008, "The Angio-Fibrotic Switch of VEGF and CTGF in Proliferative Diabetic Retinopathy" *PloS one* 3:e2675). To patients who are refractory to anti-VEGF agents, intravitreal implantation of corticosteroids may be beneficial due to corticosteroid anti-inflammatory effect; however, the ocular side effects are not uncommon.

Therefore, identifying effective therapeutic agents for targeting POA without affecting normal retinal vascularization and for those who are refractory to anti-VEGF therapy is critically needed.

SUMMARY OF THE INVENTION

In one aspect, the invention relates to a method for treating an eye disease and/or an eye disorder associated with pathological ocular angiogenesis (POA). The method comprises administering an isolated recombinant polypeptide comprising an amino acid sequence that is at least 80% identical to thrombomodulin domain 1 (TMD1) to a subject in need thereof, wherein the length of the recombinant polypeptide is no more than 200 amino acid residues.

In another aspect, the invention relates to a method for treating an eye disease and/or an eye disorder associated with VEGF-induced ocular angiogenesis, comprising administering a pharmacological composition to a subject in need thereof, the composition comprising: (a) an isolated recombinant polypeptide comprising an amino acid sequence that is at least 80% identical to thrombomodulin domain 1 (TMD1), wherein the length of the recombinant polypeptide is no more than 200 amino acid residues; and (b) a pharmaceutically acceptable carrier.

In one embodiment, the eye disease and/or an eye disorder is at least one selected from the group consisting of retinopathy of prematurity (ROP), diabetic retinopathy (DR), age-related macular degeneration (AMD), and corneal neovascularization (CNV).

In another embodiment, the administering step is performed by an intravitreal injection or by a topical application via eye drops and/or eye ointment.

In another embodiment, the recombinant polypeptide comprises an amino acid sequence that is at least 90% identical to TMD1.

In another embodiment, the recombinant polypeptide comprises the TMD1.

In another embodiment, the recombinant polypeptide consists essentially of TMD1.

In another embodiment, the recombinant polypeptide consists of TMD1.

In another aspect, the invention relates to a method of suppressing ocular vaso-obliteration and neo-vascularization associated with pathological ocular angiogenesis.

Yet in another aspect, the invention relates to a method for treating an eye disease and/or an eye disorder associated with hypoxia-inducible factor-1α (HIF-1α)-vascular endothelial growth factor (VEGF) pathway; comprising: administering an isolated recombinant polypeptide comprising an amino acid sequence that is at least 80% identical to thrombomodulin domain 1 (TMD1) to a subject in need thereof, wherein the length of the recombinant polypeptide is no more than 200 amino acid residues.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
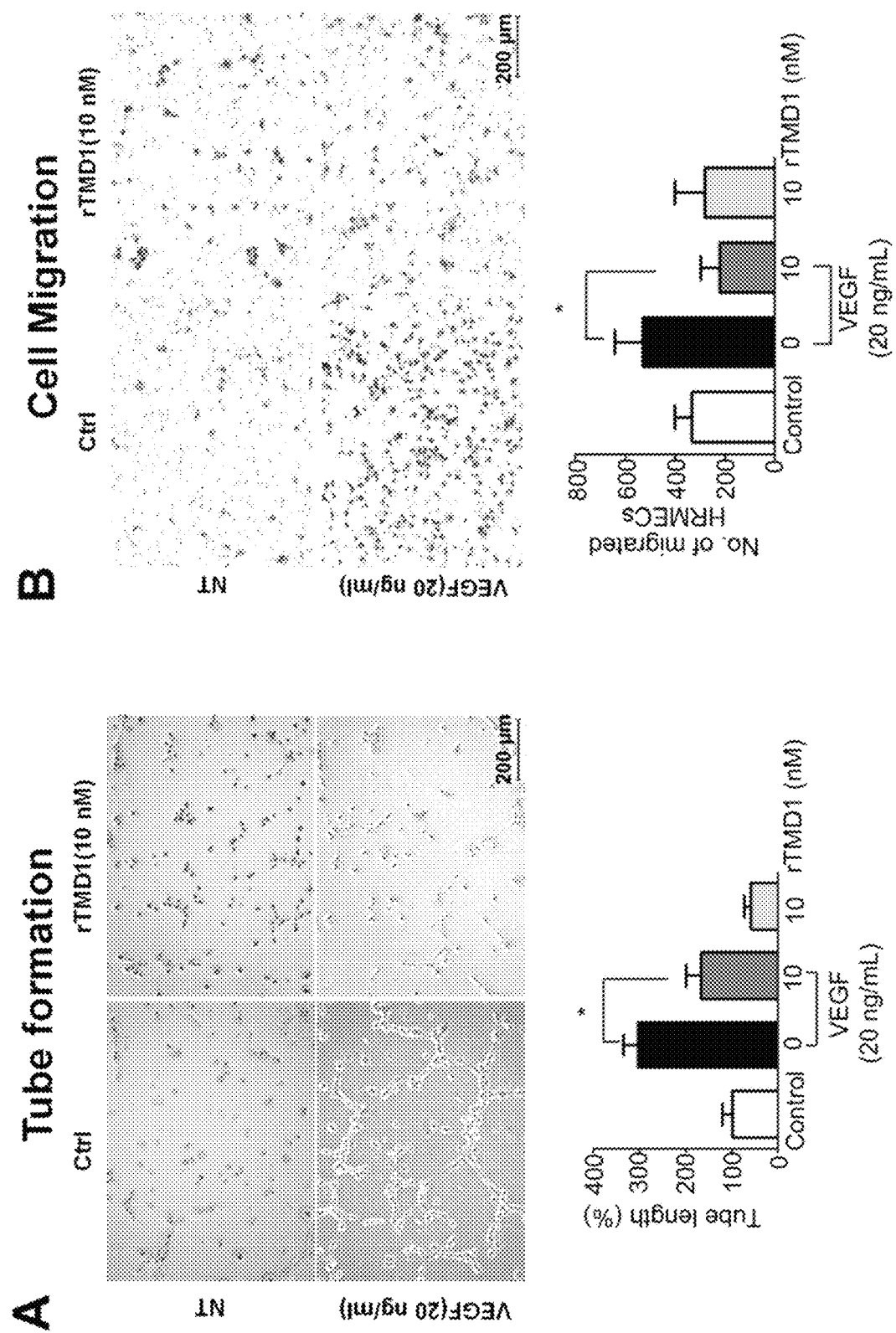
FIG. 1 shows that rTMD1 inhibited VEGF-induced angiogenesis in vitro. (A) Photomicrographs (upper panel) and a bar graph (lower panel) illustrating that rTMD1 inhibited VEGF-induced tube formation on Matrigel. The data are the mean±SD, (n=3). *P<0.01 (lower panel), (B) Photomicrographs (upper panel) and a bar graph (lower panel) illustrating that rTMD1 inhibited VEGF-induced cell migration. Values are the mean±SD (n=5), P<0.05. NT: non-treated (0 ng/ml of VEGF).

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or"treatment" refers to administration of an effective amount of a therapeutic agent to a subject in need thereof. Such a subject can be identified by a health care professional based on results from any suitable diagnostic method.

"An effective amount" refers to the amount of an active agent that is required to confer a therapeutic effect on the treated subject. Effective doses will vary, as recognized by those skilled in the art, depending on route of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$\text{HED animal dose in mg/kg} \times (\text{animal weight in kg/human weight in kg})^{0.33}.$$

As used herein, when a number or a range is recited, ordinary skill in the art understand it intends to encompass an appropriate, reasonable range for the particular field related to the invention.

By about 0.2-1000 mg it meant that all tenth and integer unit amounts within the range are specifically disclosed as part of the invention. Thus, 0.2, 0.3, 0.4 and 1, 2, 3, 4, . . . 999.7, 999.8, 999.9 and 1000 unit amounts are included as embodiments of this invention.

Normoxia shall mean normal levels of oxygen.

ICAM-1 (Intercellular Adhesion Molecule 1) also known as CD54 (Cluster of Differentiation 54) is a protein that directly contributes to inflammatory responses within the blood vessel.

Abbreviations: Vascular endothelial growth factor, VEGF; Thrombomodulin, TM; Thrombomodulin domain 1, TMD1; Thrombomodulin domain 2, TMD2; Thrombomodulin domain 3, TMD3; Thrombomodulin domain 4, TMD4; Thrombomodulin domain 5, TMD5; epidermal growth factor, EGF; serine, Ser; threonine, THr; Human retina microvascular endothelial cells, HRMECs; postnatal day 7, P7; intraperitoneal injection, IP or I.P.; vaso-obliteration, VO; neo-vascularization, NV.; pathological ocular angiogenesis, POA; oxygen-induced retinopathy (OIR); Day 1, D1; Day 4, D4; Control, CTL; wild type, WT; transgenic mice with deleted TMD1 of TM protein (or TM lectin-like domain deleted mice), ($TM^{LeD/LeD}$); N-terminal lectin-like domain, D1; Phosphate buffered saline with TWEEN® 20; PBST; B-cell lymphoma 2, BCL2; BCL-2 Associated X protein, BAX; interleukin 6, IL-6; Intercellular Adhesion Molecule 1, ICAM-1; Hypoxia-inducible factor 1-alpha, HIF-1α; partial pressure of oxygen, PO2.

Thrombomodulin (TM) is a cell surface-expressed transmembrane glycoprotein which is originally identified on vascular endothelium. TM protein has 557 amino acids, and its structure consists of 5 domains including a highly charged N-terminal lectin-like domain (D1; 1-155), a domain with six epidermal growth factor (EGF)-like structures (D2; 223-462), a serine and threonine-rich domain (D3; 463-497), a transmembrane domain (D4; 498-521) and a cytoplasmic domain (D5; 522-557).

The biologic significance of the interaction between rTMD1 and VEGF-induced POA has never been investigated. The present application discloses the finding of the anti-angiogenic effect of rTMD1 in VEGF-induced POA.

The amino acid (aa) and nucleotide (at) sequences of TMD1 are listed in SEQ ID Nos. 1 and 2, and TM in SEQ ID Nos. 3 and 4, respectively, Methods and Materials Animals C57BL6 mice were purchased from a local vendor in Taiwan. N-terminal lectin-like domain of thrombomodulin deleted ($TM^{LeD/LeD}$) mice was a gift from Dr. Conway (Conway, E. M. 2012. "Thrombomodulin and its role in inflammation" Seminars in immunopathology 34:107-125). Both male and female mouse pups were used. The body weight of the mice used in the experiments ranged from 5-7 gram.

Preparation of rTMD1 Proteins rTMD1 expression and purification in the Pichia pastoris expression system was conducted as previously described by Shi et al (2008) (Lectin-like domain of thrombomodulin binds to its specific ligand Lewis Y antigen and neutralizes lipopolysaccharide-induced inflammatory response. Blood 112:3661-3670). A Pichia pastoris pPICZα vector containing a polyhistidine (6×His) tag and c-Myc epitope for protein detection and purification was used to express and secret human rTMD proteins in Pichia pastoris. Purified rTMD1 proteins were examined by sodium dodecyl sulfate-polyacrylamide gel electrophoresis (SDS-PAGE) and Western blotting.

Cell Cultures

Human retina microvascular endothelial cells (HRMECs) purchased from Applied Cell Biology Research Institute were grown hi medium 199 supplemented with 20% fetal bovine serum and endothelial cell growth supplement (Millipore, Bedford). Experiments were performed with cells between passages 2 and 4.

Tube Formation Assay

To analyze the effect of rTMD1 on VEGF-mediated endothelial tube formation in vitro, HRMECs were starved for 12 hours in M199 containing 1% FBS and then preincubated with rTMD1 (10 nM) in the presence or absence of VEGF (20 ng/ml) for 24 hours. The total tube length was measured using METAMORPH® software (Molecular Device) and compared with a control.

Cell Migration Assay

Cell migration was measured by Boyden chamber assays with 0.1%, gelatin coated, 48-multiwell, 8-µm pore-size polycarbonate filters. To analyze the inhibitory effect of rTMD1 on VEGF-promoted cell migration, HRMECs were starved for 12 hours in M199 containing 1% FBS, then preincubated with rTMD1 (10 nM) in the presence or absence of VEGF (20 ng/ml) for 24 hours before being placed in the upper compartment, and 5% M199 was added to the bottom compartment as chemoattractant. Migrated cells were stained with Liu's stain and the numbers were counted.

Cell Viability Assay

Water-Soluble Tetrazolium salt-1 (WST-1) proliferation assay was used to evaluate the effect of rTMD1 on cell viability of HRMECs. PBS was used as a control. Absorbance was measured at 450 nm using a plate reader, and absorption at 630 nm was measured as a background.

Western Blot Analysis

Approximately 10 µg of total protein was separated via 10% SDS-PAGE and transferred onto a polyvinylidene difluoride membrane. The membranes were blocked with 5% nonfat milk powder for 1 h at room temperature. After being probed with specific antibodies against TM, ERK, AKT, JNK, P-38, VEGF, hypoxia-inducible factor-1α (HIF-1α), and β-actin at 4° C. overnight, the membranes were incubated with peroxidase-conjugated specific secondary antibodies for 1 h at room temperature. The signal was detected by enhanced chemiluminescence reagent (Millipore) and a Fujifilm LAS-3000 imager.

Experimental Oxygen-Induced Retinopathy Animal Model

Oxygen-induced retinopathy (OIR) was generated as previously described. In brief, neonatal mice were exposed to 75% oxygen from postnatal day 7 (P7) to P12 and returned to room air (21% oxygen) from P12 to P17. During the first phase of hyperoxic exposure (P7-P12), retinal vessels constrict to regulate retinal $PO_2$ levels, and immature capillaries in the central retina regress leading to a central zone of vaso-obliteration (VO). After being moved from 75% oxygen chamber to room air at P12, the formation of neovascularization (NV) in the retina was at maximum at P17. The mice were sacrificed at P17. Mice were administered rTMD1, PBS, or bevacizumab via I.P. once a day between P13 and P16. Quantification of oxygen-induced retinopathy was measured by outlining VO and NV structures using ADOBE® PHOTOSHOP® and comparing total VO and NV area with the total retinal area (Connor et al, Nat Protoc 4(11) (2009) 1565-73).

Histology and Immunofluorescent Staining

Mouse eyeballs were enucleated, fixed in paraformaldehyde (4%) for hour, the corneas and muscles were removed, and eyecups were placed in paraformaldehyde for another 1 hour. The entire retina was dissected from the eyecup, rinsed, blocked, and then incubated with primary antibodies or conjugated secondary antibodies overnight at 48° C. After rinsing with phosphate buffered saline with TWEEN® (PBST), the retinas were flat-mounted on cover slides with aqueous mounting medium. Other retinas were cut into sections with thickness of 20-µm using LEICA® CM 1800 Cryostat. After washing and blocking, the flat-mounted retinas or cryostat sections were incubated with primary antibodies overnight at 48° C. The secondary antibodies were added for 1 hour at room temperature, and the nuclei were counterstained with DAPI staining solution. The cryostat sections and flat-mounts were incubated with the following antibodies: fluorescein-labeled isolectin B4 (1:150 dilution: VECTOR® Laboratories), DYLIGHT™ 594 labeled isolectin B4 (1:150 dilution; VECTOR® Laboratories), HIF-1α (1:100 dilution; Novus Biologicals), VEGF (1:100 dilution; Proteintech), BAX (1:100 dilution; Taiclone), and BCL-2 (1:100 dilution; Santa Cruz Biotechnology).

Terminal Deoxynucleotidyl Transferase (TdT) dUTP Nick End Labeling (TUNEL) Assay Normoxia or OIR mice were treated with rTMD1 or PBS i.p. and sacrificed at P17. Enucleated globes were fixed in paraformaldehyde (4%) and embedded in paraffin. TUNEL staining, also called TUNEL assay, was performed and TUNEL-positive (apoptotic) cells were evaluated in three randomly selected fields at 200× magnification under a light microscope (Carl Zeiss, Chester, Va., USA). Each group has at least six animals.

In Vitro Cobalt Binding Assay

HRMECs were cultured in serum-free M199 to starve overnight, and then treated with $CoCl_2$ (400 µM) and rTMD1 (20 nM) for 6 hours. The cell lysates were collected and stored at −80° C. for Western Blot analysis to confirm the expression of HIF-1α and VEGF.

Quantitative Real-Time PCR (qRT-PCR)

Total RNAs of mouse retinas under group-specified experimental conditions were extracted and qR-T-PCR was performed using SYBR™ Green RT-PCR Master Mix (BIOTOOL™, Houston). Expression of target genes was normalized to β-actin and measured in triplicate. The 2-ΔΔCq method was used to calculate target gene expression. The PCR primers were designed based on the NCBI GENBANK® database.

Statistical Analysis

Comparisons between two groups were analyzed by two-tail Student's t tests. For comparisons more than 2 groups, 1-way ANOVA followed by a Bonferroni multiple comparison test were used. Probability values less than 0.05 were considered statistically significant. All statistical analyses were performed using GraphPad Prism 6.0 software.

Results

Inhibitory Effects of rTMD1 on VEGF-Mediated HRMEC Migration and Tube Formation

To explore the effects of rTMD1 on VEGF-mediated pathological ocular angiogenesis (POA), HRMECs were treated with rTMD1 in the presence of VEGF (FIG. 1A-B). The results show that VEGF-mediated tube formation (FIG. 1A) and cell migration (FIG. 1B) were inhibited by rTMD1.

rTMD1 Suppressed Pathological Ocular Angiogenesis (POA) in Oxygen-Induced Retinopathy (OIR)

Figure 2:
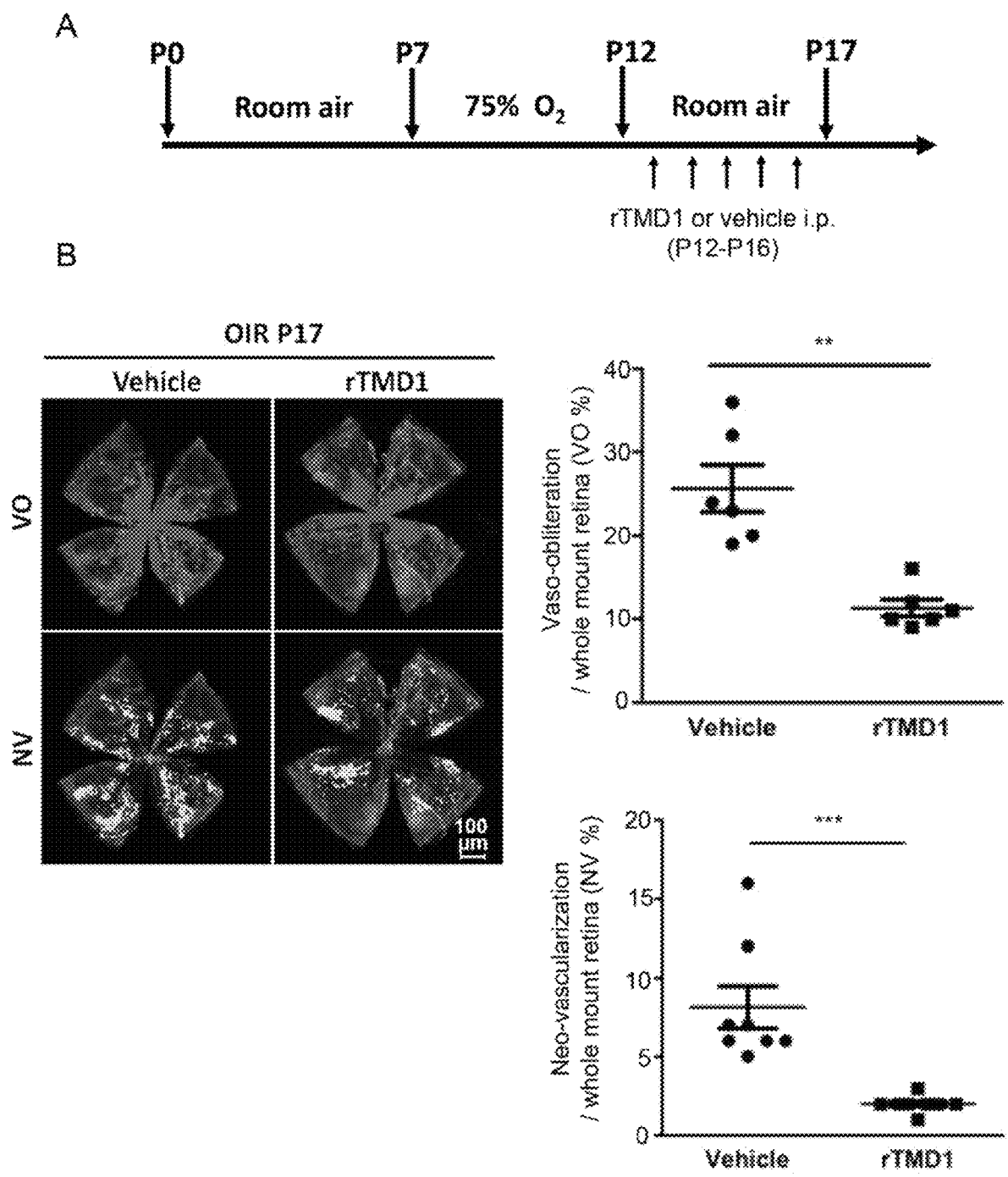
FIG. 2 shows that rTMD1 rescued POA in vivo. (A) A schematic drawing illustrating a time course for inducing oxygen-induced retinopathy (OIR). (B) Photomicrographs (left panel) and dot plots (right panels) illustrating rTMD1 significantly suppressed hypoxia-induced vaso-obliteration (upper right panel) and neovascular (lower right panel) tufts in a murine OIR model. Values are expressed as the mean±SD (n=6-8 retinas per group), P<0.01 and *P<0.001.
Figure 3:
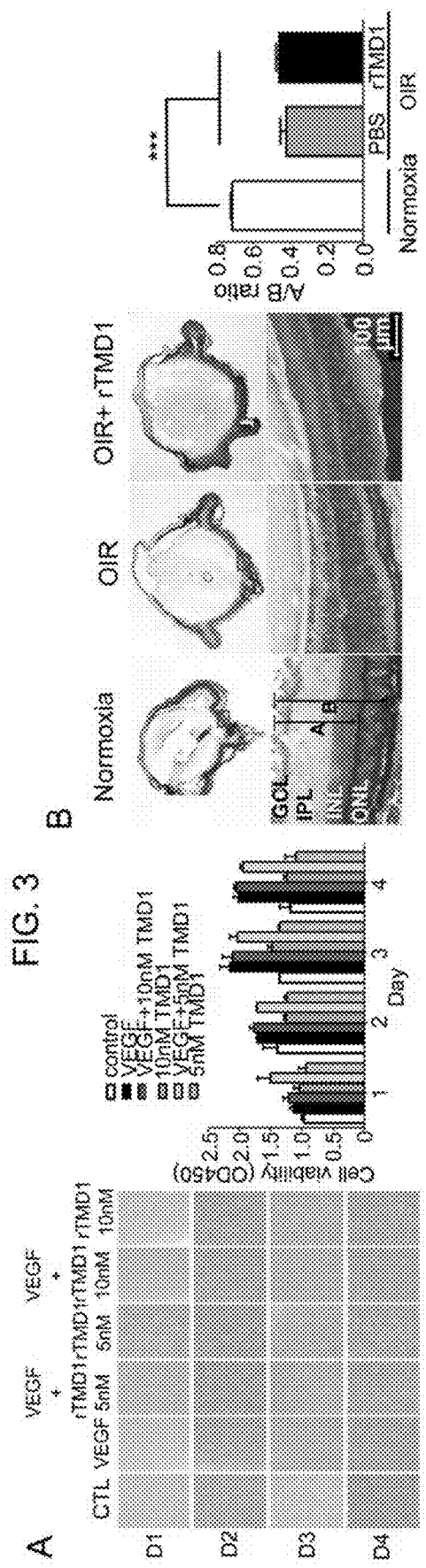
FIG. 3 shows that rTMD1 treatment does not induce cell toxicity and suppress apoptosis in OIR. (A) Photomicrographs (left panel) and a bar graph illustrating the effect of rTMD1 on the cell viability of HRMECs in the presence or absence of VEGF (20 ng/ml). (B) Photographs of H&E staining (left panel) and a bar graph (right panel) illustrating that rTMD1 (1600 µg/Kg) does not affect the retinal thickness in OIR mouse model. INL, inner nuclear layer; ONL, outer nuclear layer. ***P<0.001. (C) Photographs of TUNEL staining of retina from OIR mouse treated with PBS (upper panel) or rTMD1 (lower panel). Arrows indicate TUNEL-positive cells. Magnification 200×. (D) Photomicrographs illustrating the effects of rTMD1 on the retina BAX and BCL expression levels in OIR mouse model.
Figure 3:
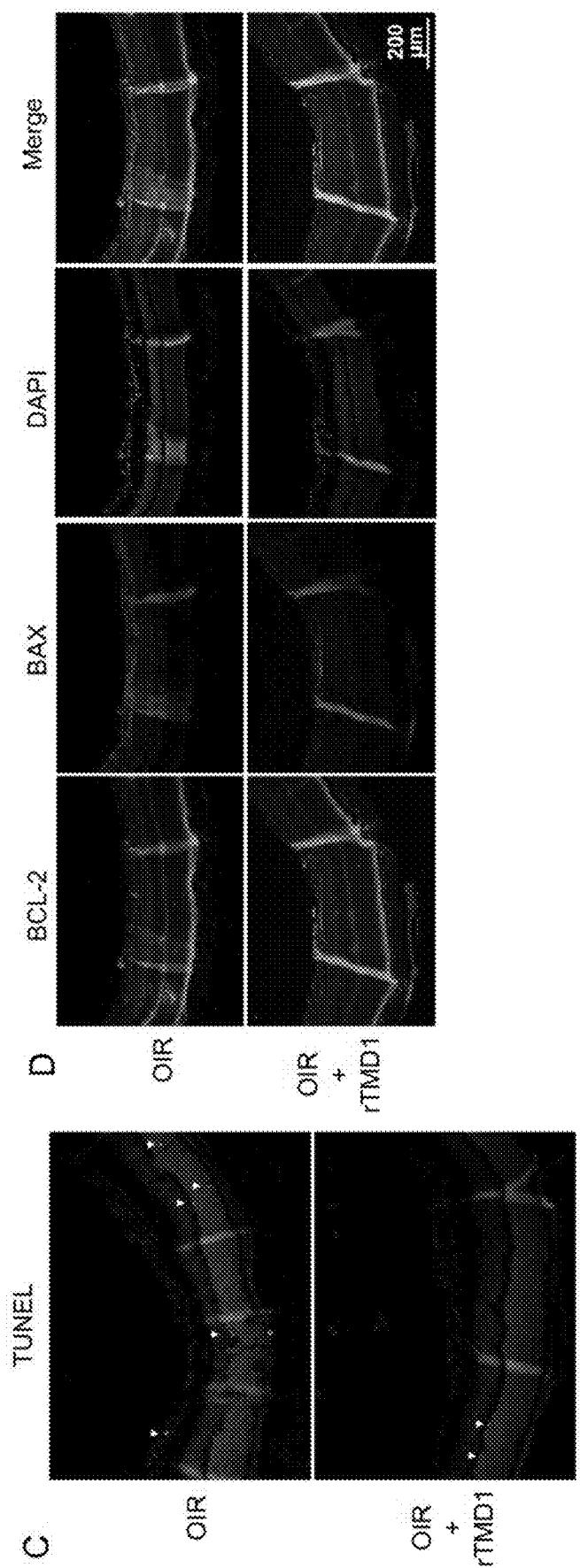

To evaluate the effect of rTMD1 in OIR animal model, OIR mice were injected daily via I.P. with rTMD1 (0.8 mg/kg) or vehicle according to the schedule shown in FIG. 2A and the retinal wholemount staining was analyzed. The results show that rTMD1 suppressed hypoxia-induced vaso-obliteration (VO) and neovascular (NV) tufts (FIG. 2B, left panel) in a murine OIR model. The suppressions in VO and NV by the rTMD1 treatment were significant as compared to the vehicle treatment (FIG. 2B, upper and lower right panels).

rTMD1 Treatment Did not Induce Cell Toxicity but Suppressed Apoptosis in OIR Mice The cytotoxicity of rTMD1 on HRMECs was evaluated by WST-1 assay (FIG. 3A) rTMD1 did not affect the cell viability of HRMECs (FIG. 3A left and right panels). To evaluate the retinal structure changes, H&E staining was performed (FIG. 38, left panel). The retinal thickness A (internal limiting membrane to the inner nuclear layer) to B (internal limiting membrane to the outer nuclear layer) ratio was measured at P17 under different conditions, including normoxia, OIR, and OIR+rTMD1 (1.6 mg/Kg) (FIG. 3B left panel). The retinal thickness A/B ratio was significantly decreased in OIR mice as compared to normoxia mice, while rTMD1 (1600 µg/Kg) did not affect the retinal thickness of OIR mice (FIG. 3B, right panel, ***P<0.001).

We determined whether rTMD1 could provide additional anti-apoptotic effects on retinas in OIR mice. Immunofluorescent TUNEL staining was performed in retina sections and apoptotic cells were counted on three randomly selected fields (×200) per section. The number of TUNEL-positive cells decreased significantly in all the retinal layers in the OIR mice treated with rTMD1 as compared with the OIR mice untreated with rTMD1 (FIG. 3C). Immunofluorescent staining methods for apoptotic markers BCL-2 and BAX were performed to determine the anti-apoptotic effect of rTMD1 in the OIR mice (FIG. 3D). The results indicate that rTMD1 treatment increased the expression level of BCL-2 but decreased the expression level of BAX in the retina of OIR mice (FIG. 3D). Figures were representative of three independent experiments. Together, these data suggested that rTMD1 did not induce direct cytotoxicity to retinal cells and afforded an additional protective effect.

TMD1 Deficiency Increased POA in OIR

To further confirm the role of rTMD1 in POA, retinal angiogenesis was investigated in WT and TM$^{LeD/LeD}$ mice in normoxia and hyperoxia, respectively. The impact of TMD1 deficiency was examined by comparing retinal vasculature in C57/BL6 (wild type) and TMD1 knockout (TM$^{LeD/LeD}$) mice housed in normoxia (normoxic mice) or exposed to hyperoxia (hyperoxic or OIR mice). Retinal flat mounts were stained with isolectin (green) to visualize vessels, vaso-obliteration areas pseudo-colored red and tufts pseudo-colored yellow. Fat-mounted retinas from normoxic TM$^{LeD/LeD}$ mice revealed normal retinal vasculature with similar levels of vascularized retinal areas as compared to normoxic WT mice. There was no detectable developmental difference in vascular growth between C57BL6 and TM$^{LeD/LeD}$ mice housed in normoxia at P7, P12, and P25 (FIG. 4A, left and right panels), which indicates that that TMD1 is likely dispensable for physiological development of retinal angiogenesis in normoxia.

Figure 4:
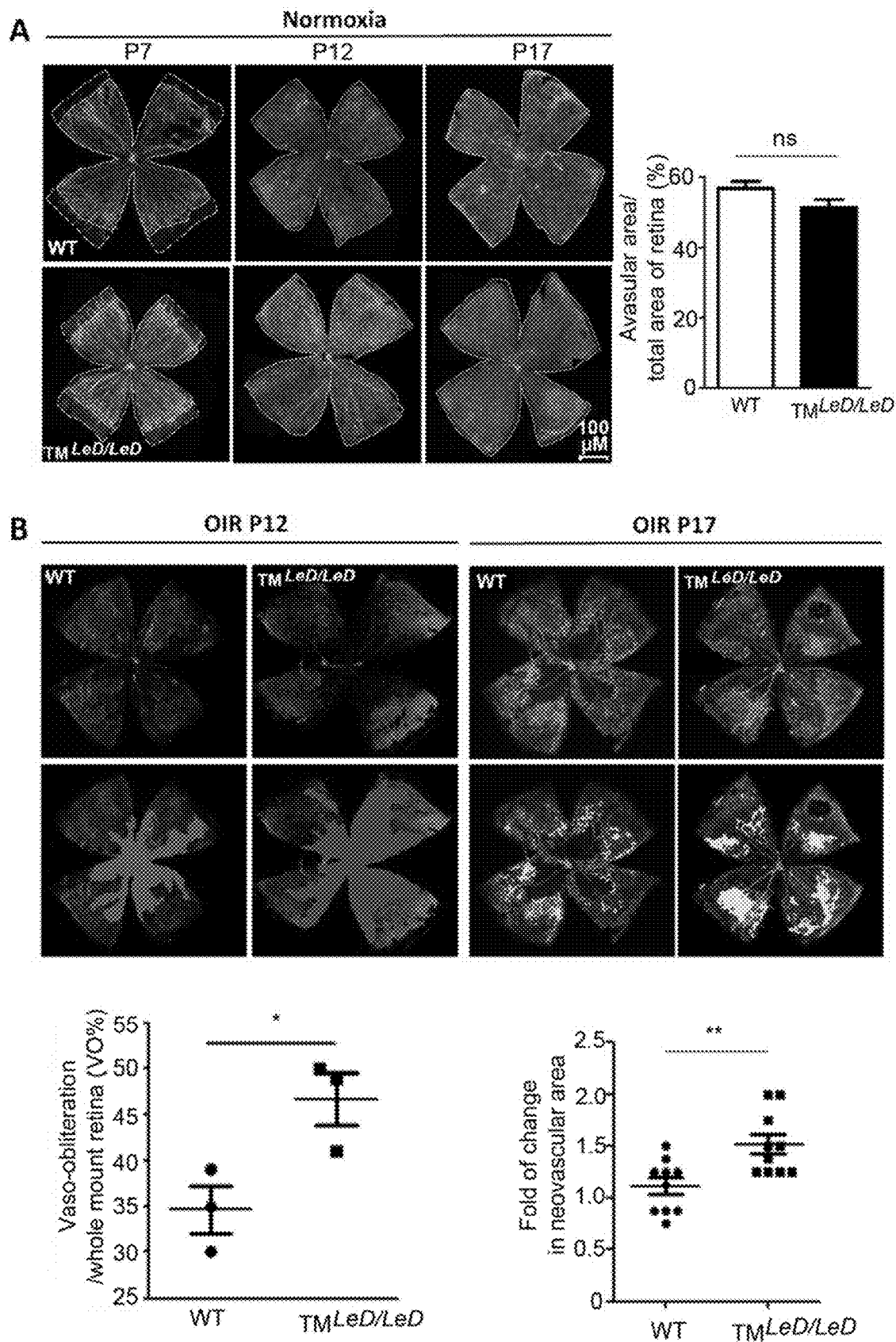
FIG. 4 shows that TMD1 deficiency increased POA in OIR. (A) Photomicrographs (left panel) illustrating the vascular areas of retinas in WT and mice at normoxia P7, P12 and P17, and a bar graph (right panel) illustrating that retinal vascular growth was not affected in $TM^{LeD/LeD}$ mice at normoxia P17. Values are the mean±SD. n=4 per group, (B) Photomicrographs illustrating changes in vascular areas of retinas in WT and $TM^{LeD/LeD}$ mice at OIR P12 and OIR 17 (upper panel), and dot plots illustrating vaso-obliteration at P12 (lower left panel) and fold change in neovascular area (lower right panel) at P17 in OIR mice of wild type and $TM^{LeD/LeD}$ (n=3-10 retinas per group). Data are the mean±SD, *P<0.05 and **P<0.01.

In OIR WT and TM$^{LeD/LeD}$ mice pathological changes in the retinal vessels were observed at OIR P12 and P17 as having vaso-obliteration (VO) and abnormal neovascularization (NV) tufts (FIG. 4B, tipper panel). The OIR-induced VO (FIG. 4B, lower left panel) and NV (FIG. 4B, lower right panel) were significantly enhanced in the TM$^{LeD/LeD}$ mice at DIR P17.

rTMD1 Regulates VEGF Expression Via HIF-1α In Vitro and In Vivo

Figure 5:
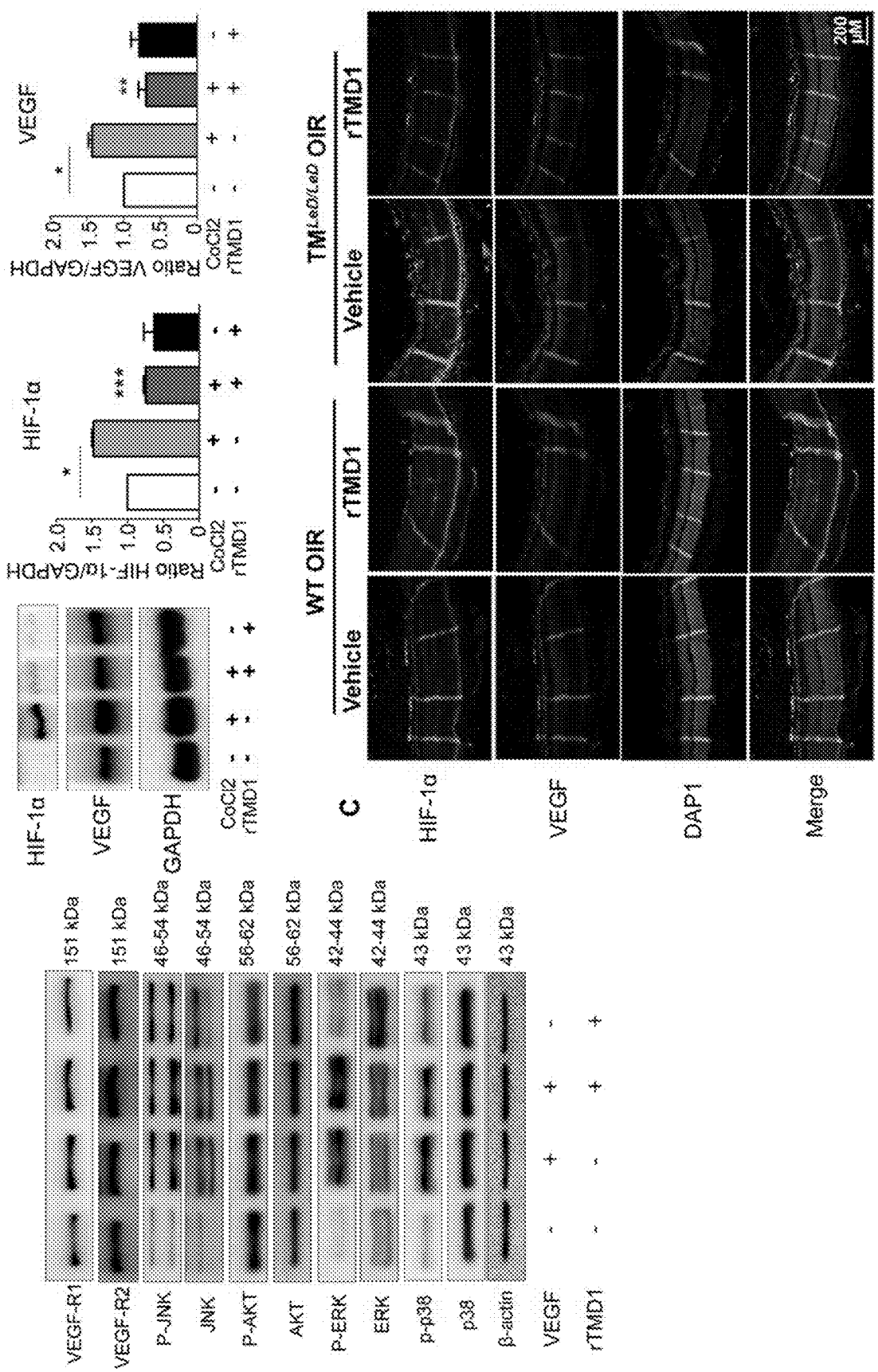
FIG. 5 shows that rTMD1 inhibits HIF-1α protein expression in vitro and in vivo. (A) a Western blot image illustrating the expression levels of VEGF receptors and its downstream factors in the presence and absence of rTMD1 and VEGF. (B) a Western blot image (left panel) and bar graphs (middle and right panels) illustrating that rTMD1 significantly inhibited cobalt chloride (400 µM) induced HIF-1α and VEGF expression levels in vitro. Values are the mean±SD (n=5). *P<0.05, P<0.01 and *P<0001. (C) Photomicrographs of immunofluorescence staining of retinas from WT OIR and $TM^{LeD/LeD}$ OIR mice at P17, illustrating that rTMD1 (0.8 mg/Kg) inhibited HIF-1α and VEGF expression levels in vivo. Similar results were obtained in at least 3 different experiments.

We investigated whether rTMD1 has a direct effect on VEGF by examining the expression levels of VEGF's receptors and downstream signaling pathway factors including JNK, AKT, ERK, and p38 in the presence and absence of VEGF (20 ng/ml). The results indicate that rTMD1 (10 nM) did not have effects on VEGF (20 ng/ml)-induced expression levels of VEGF receptors and its downstream factors (FIG. 5A).

We therefore Investigated other factors that might regulate VEGF expression. It has been reported that the HIF-1α-VEGF pathway plays an important role in retinal neovascularization, and that the expression of HIF-1α is upregulated at P17 in OIR. We investigated whether rTMD1 could regulate the HIF-1α-VEGF pathway. A cobalt binding assay was used to mimic a hypoxia condition. HRMECs were incubated with $CoCl_2$ (400 µM) in the presence or absence of rTMD1 (20 nM) for 6 hours. The Western blot image (FIG. 5B, left panel) indicate that $CoCl_2$ induced the protein expression of HIF-1α and also significantly upregulated the protein level of VEGF. The upregulation of both HIF-1α and VEGF induced by $CoCl_2$ was significantly inhibited by rTMD1 (FIG. 5B, middle and right panels).

Figure 6:
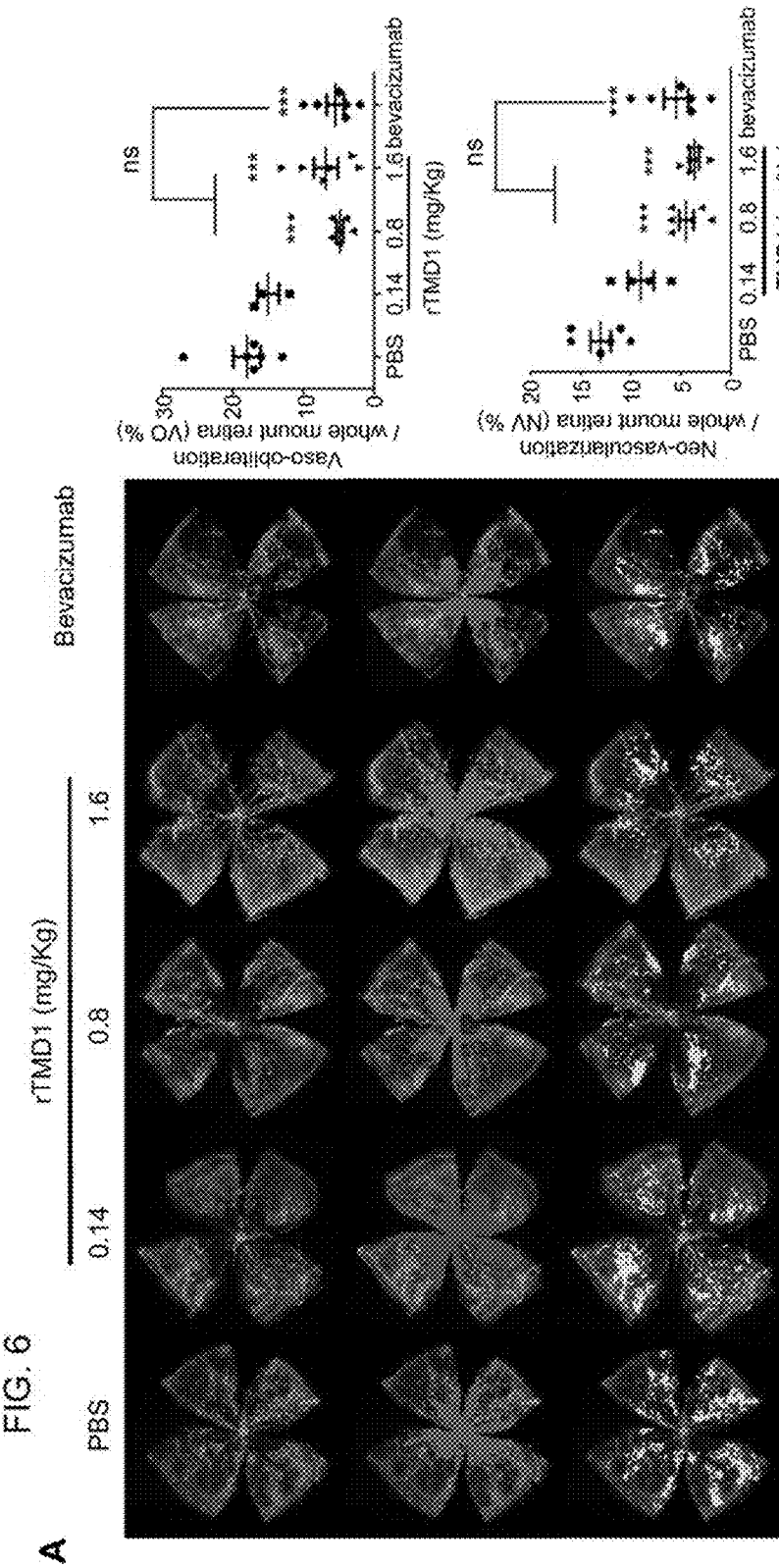
FIG. 6 shows that rTMD1 has therapeutic effects comparable to bevacizumab and possesses additional anti-inflammatory effects. (A) Photomicrographs (left panel) and dot plots (upper right and lower right panels) illustrating retinas from OIR P17 mice treated with PBS, rTMD, or bevacizumab (5 mg/Kg). (B) Bar graphs illustrating the effects of rTMD1 (0.8 mg/Kg) and bevacizumab (5 mg/Kg) on the mRNA levels of HIF-1α, VEGF, IL-6 and ICAM-1 in normoxia and OIR P17 mice, respectively. Values are the mean±SD (n=3-6 per group). *P<0.05, P<0.01 and *P<0.001.
Figure 6:
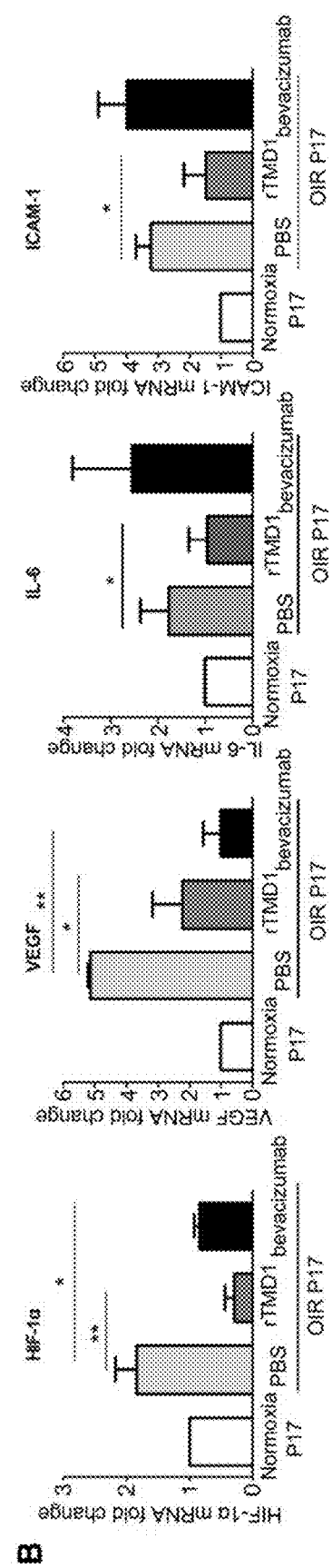

The images of immunofluorescent staining of the retinas from the OIR mice indicate that both HIF-1α and VEGF expression levels were evident in the control groups (vehicle-treated WT OIR and TM$^{LeD/LeD}$ OIR mice). The expression levels of both HIF-1α and VEGF were suppressed in the rTMD1-treated WT OIR and TM$^{LeD/LeD}$ OIR mice as compared to the vehicle-treated WT OIR and TM$^{LeD/LeD}$ OIR mice (FIG. 5C).

rTMD1 is Comparable to Bevacizumab and Exhibits Additional Anti-Inflammatory Effects To evaluate the therapeutic potential of rTMD1 in pathological ocular angiogenesis (POA), the effects of rTMD1 on POA were compared to the current widely used anti-VEGF agent bevacizumab. The results indicate that both rTMD1 and bevacizumab can effectively reduce NV and VO in OIR P17 mice (FIG. 6A, left panel) and that the effect of rTMD1 at 0.8 mg/Kg is comparable to bevacizumab (5 mg/Kg). (P<0.05, FIG. 6A, upper and lower right panels). Because rTMD1 is well-known for its anti-inflammatory effect, the effects of rTMD1 on the gene expression of inflammatory markers in retinas in OIR mice were investigated by qRT-PCR. FIG. 6B shows that the retina mRNA levels of HIF-1α, VEGF, IL-6 and ICAM-1 were all increased or upregulated in OIR P17 mice as compared to Normoxia P17 mice. The increased or upregulated retina HIF-1α and VEGF mRNA levels in the OIR P17 mice were suppressed or downregulated in the OIR P17 mice treated with rTMD1 (0.8 mg/Kg) and in the OIR P17 mice treated with bevacizumab (5 mg/Kg). In contrast, the increased or upregulated retina IL-6 and ICAM-1 mRNA levels were suppressed (inhibited) or downregulated only in the OIR P17 mice treated with rTMD1 but not in the OIR P17 mice treated with bevacizumab. In other words, bevacizumab was ineffective in suppressing or downregulating the retina IL-6 and ICAM-1 mRNA levels in the OIR mice. Therefore, the data indicate that rTMD1 not only suppresses VEGF-induced POA but also has additional anti-inflammatory effects compared to bevacizumab.

Discussions

The present application relates to the dual anti-angiogenic (FIGS. 2B and 6A) and anti-inflammatory (FIG. 6B) effects of rTMD1 in POA. Although rTMD1 inhibited VEGF-induced cell migration and tube formation, the cell proliferation function is preserved (FIG. 1A-B), rTMD1 reduced the number of TUNEL-stained cells (FIG. 3C), increased BCL-2 (cell apoptosis suppressor) but decreased BAX (cell apoptosis inducer) protein levels in the retinas of OIR mice (FIG. 3D), suggesting a potential protective effect of rTMD1 in POA.

Unlike traditional anti-VEGF therapeutic agent, rTMD1 does not directly bind to VEGF or VEGF receptors (FIG. 5A). Hypoxia-inducible factor 1-alpha (HIF-1α), one of the upstream factors of VEGF, is the most important oxygen-dependent regulator that may lead to POA. rTMD1 suppressed the protein expression levels of HIF-1α and VEGF in the CoCl$_2$ assay and in the OIR mouse model (FIG. 5B). This suggests that rTMD1 exerts an anti-angiogenic effect through regulation of the HIF-1α-VEGF pathway, which has advantages of suppressing pathological but without affecting physiological angiogenesis. Unfortunately, none of the HIF-1α inhibitors so far have been able to be used in the real world due to the adverse reactions both locally and systemically. The present discovery that rTMD1 could inhibit VEGF-mediated POA via HIF-1α without affecting physiological angiogenesis has provided rTMD1 as a potential HIF-1α inhibitor for clinical use in treating HIF-1α-VEGF pathway-mediated diseases including POA.

rTMD1 inhibited POA without affecting physiological retinal vessel growth (FIG. 3A-B). rTMD1 reduced VEGF protein level induction in in vitro CoCl$_2$ assay of HRMECs (FIG. 5B, left and right panels) and in vivo OIR mice (FIG. 5C) through downregulation of HIF-1α protein expression (FIG. 5B, middle panel). The anti-angiogenic effect of rTMD1 is comparable to bevacizumab in OIR P17 mice (FIG. 6A). rTMD1 also afforded additional anti-inflammatory effects by attenuating expression levels of IL-6 and ICAM-1 proteins in the retina of OIR P17 mice (FIG. 6B). Therefore, rTMD1 inhibited POA without affecting physiological vessel growth and had anti-apoptotic effects that may be safe for long-term use.

rTMD1 has an additional advantage in having an anti-inflammatory effect. Angiogenesis, under both physiological and pathological situations, is usually associated with inflammation. TM$^{LeD/LeD}$ mice have been known to have more severe inflammatory responses and rTMD1 can attenuate inflammation by sequestering high mobility group box B1 (HMGB1) protein and inhibiting complement activation. Except the HMGB1, however, other molecules that interact with rTMD1 and participate in anti-inflammation are still unknown.

rTMD1 significantly reduced IL-6 and ICAM-1 expression levels in POA (FIG. 6B), which may be beneficial to patients who respond poorly to anti-VEGF agents. The IL-6 level and ICAM-1 were significantly elevated in the OIR mice treated with bevacizumab (FIG. 6B). This indicates that compared to bevacizumab, rTMD1 has an additional anti-inflammatory effect and may be beneficial for treatment of POA.

Having both anti-angiogenic and anti-inflammatory effects, rTMD1 can generate dual suppressive effects in POA Several possible limitations in clinical applications of rTMD1 have been considered. In basic research there is always a gap from the bench to clinical practice. rTMD123 (also called ART-123 or RECOMODULIN®) has been approved for treatment of disseminated intravascular coagulation in Japan and has had good long-term clinical outcomes. One can expect that rTMD1, containing only one domain, may have a more specific function and a higher chance to be applied clinically in the future.

Although recombinant protein drugs have disadvantages including the limitation in drug delivery, short half-life and high cost, the amount needed to be delivered for treating POA by an intravitreal injection is much less when compared to other organs. The recombinant protein Aflibercept has already been used for treating POA and thus, rTMD1 may also possess the potential as a therapeutic agent.

In summary, in oxygen induced retinopathy (OIR) animal model, rTMD1 treatment significantly decreased retinal neovascularization but spares normal physiological vessel growths. Loss of TMD1 significantly promoted POA in OIR. Hypoxia-inducible factor-1α, the transcription factor located on the upstream of VEGF, was suppressed after rTMD1 treatment. The levels of interleukin-6 ($p<0.001$) and intercellular adhesion molecule-1 ($p<0.001$) were also significantly suppressed. Therefore, rTMD1 suppressed POA via inhibition of a HIF-1α-VEGF pathway and reduced inflammation via inhibition of retina IL-6 and ICAM-1 in the mice of OIR. These results suggest that rTMD1 has dual effects in suppressing pathological angiogenesis and inflammation in OIR, thus rTMD1 may be a potential therapeutic agent for POA.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for treating an eye disease and/or an eye disorder associated with pathological ocular angiogenesis (POA); comprising:
administering an isolated recombinant polypeptide comprising an amino acid sequence that is at least 80% identical to thrombomodulin domain 1 (TMD1 ; SEQ ID NO: 1) to a subject in need thereof, wherein the length of the recombinant polypeptide is no more than 200 amino acid residues, and further wherein the POA is vascular endothelial growth factor (VEGF)-induced POA.

2. The method of claim 1, wherein the eye disease and/or an eye disorder is at least one selected from the group consisting of retinopathy of prematurity (ROP), diabetic retinopathy (DR), age-related macular degeneration (AMD), and corneal neovascularization (CNV).

3. The method of claim 1, wherein the administering step is performed by an intravitreal injection or by a topical application via eye drops and/or eye ointment.

4. The method of claim 1, wherein the isolated recombinant polypeptide comprises an amino acid sequence that is at least 90% identical to TMD1 (SEQ ID NO: 1) and is no more than 200 amino acid residues in length.

5. The method of claim 1, wherein the isolated recombinant polypeptide comprises the amino acid sequence of TMD1 (SEQ ID NO: 1) and is no more than 200 amino acid residues in length.

6. The method of claim 1, wherein the isolated recombinant polypeptide consists essentially of TMD1 (SEQ ID NO: 1) and is no more than 200 amino acid residues in length.

7. The method of claim 1, wherein the isolated recombinant polypeptide consists of TMD1 (SEQ ID NO: 1).

* * * * *